Figures 1A, 1B:
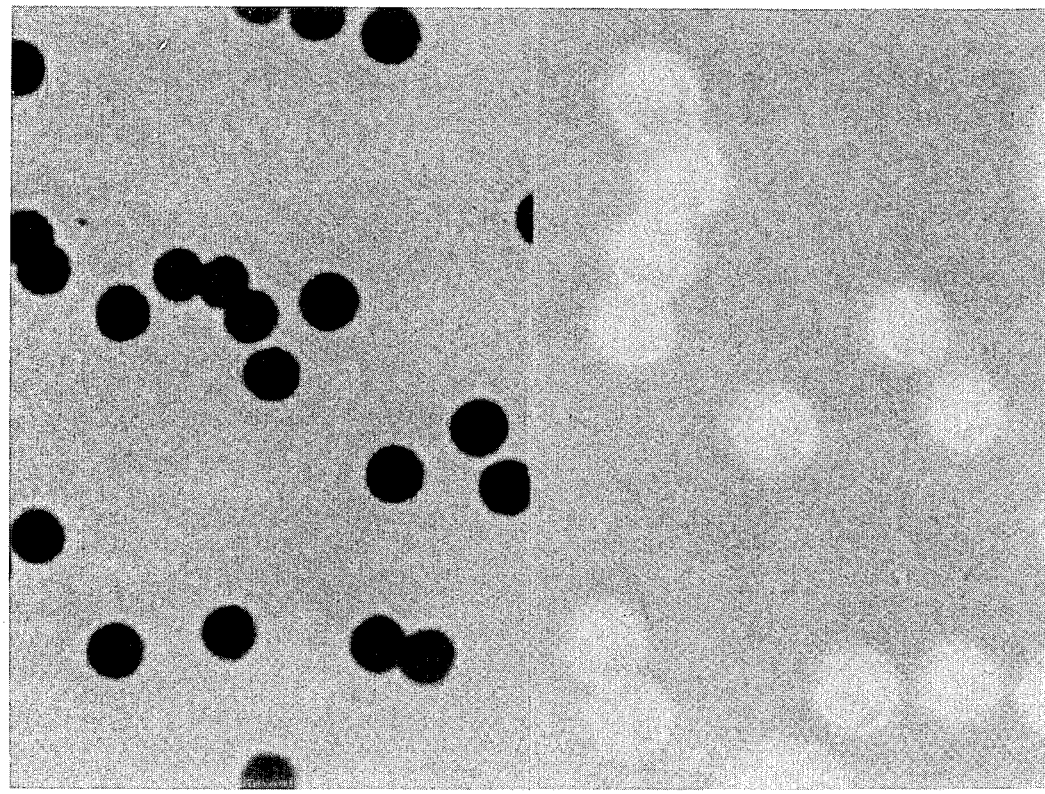
Figure 2:
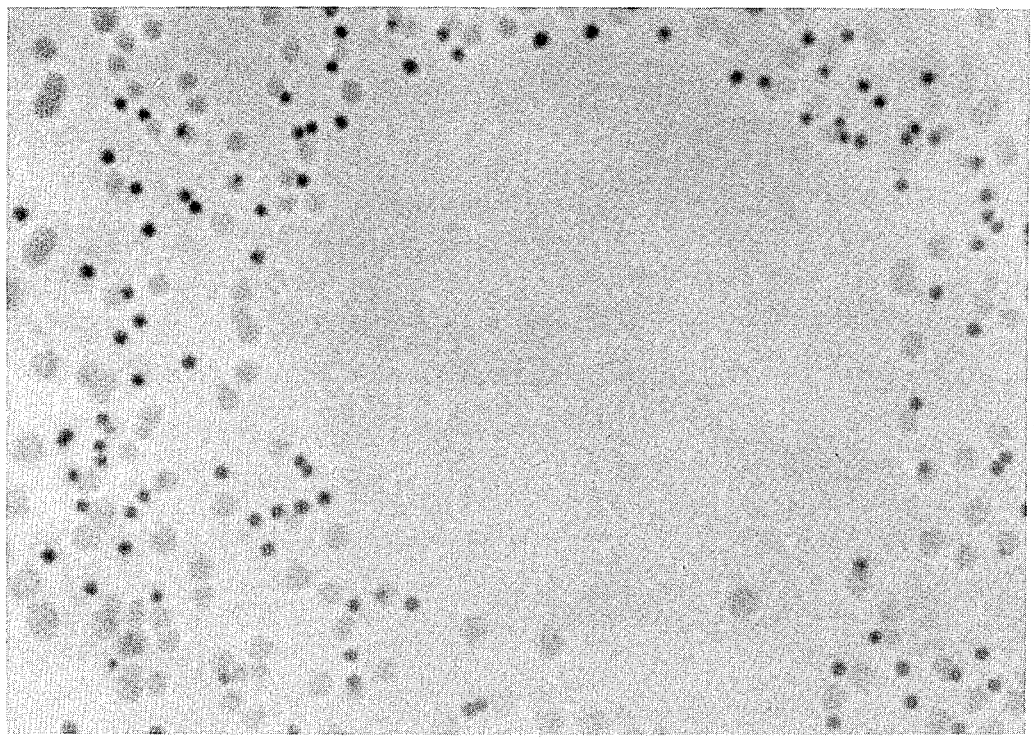

United States Patent [19]

Bhaduri et al.

[11] Patent Number: 4,952,497
[45] Date of Patent: Aug. 28, 1990

[54] SIMPLE AND RAPID METHOD FOR DETECTION OF VIRULENT *YERSINIA ENTEROCOLITICA*

[75] Inventors: Saumya Bhaduri, Warminster; Lucille K. Conway, Sellersville, both of Pa.; Reynato V. Lachica, Natick, Mass.

[73] Assignee: The United States of America as represented by the Secretary of Agriculture, Washington, D.C.

[21] Appl. No.: 140,501

[22] Filed: Jan. 4, 1988

[51] Int. Cl.$^5$ .................. C12Q 1/00; C12Q 1/02; G01N 33/48; G01N 1/30

[52] U.S. Cl. .................. 435/34; 435/29; 435/6; 435/39; 435/320; 435/822; 436/63; 436/164; 424/3; 424/7.1

[58] Field of Search .................. 435/4, 5, 6, 29, 34, 435/38, 39, 235, 320, 822; 436/63, 164; 424/7.1, 3

[56] References Cited

U.S. PATENT DOCUMENTS 4,225,669 9/1980 Melmick et al. .................. 435/29

OTHER PUBLICATIONS

Stern et al., *Journal of Food Science*, vol. 47, pp. 582–584 (1982).
Davis et al., *Microbiology*, 2nd ed., pp. 92 & 93, Harper & Row, Hagerstown, Md. (1973).
Prpic et al., *Journal of Clinical Microbiology*, vol. 22(1), pp. 105–110 (May, 1985).
D. L. Zink et al., "*Yersinia Enterocolitica* and *Yersinia Enterocolitica*-like Species: Their Pathogenicity and Significance in Foods," J. Food Safety Y: 223–241 (1982).
B. Swaminathan et al., "A Review of *Yersinia enterocolitica*," J. Appl. Bacterio, 1. 52 151–183 (1982).
J. L. Ferreira et al., "Detection of Entrotoxigenic *Escherichia coli* in Foods by DNA Colony Hybridization," J. Food Sci. 51: 665–667 (1986).
J. J. Jagow et al., "Enumeration by DNA Colony Hybridization of Virulent *Yersinia enterocolitica* Colonies in Artificially Contaminated Food," Appl. Environ. Microbiol. 51: 441–443 (1986).
D. A. Sack et al., "Test for Enterotoxigenic *Escherichia coli* Using Y1 Adrenal Cells in Miniculture," Infect. Immun. 11: 334–336 (1975).
R. H. Yolken et al., "Enzyme-Linked Immunosorbent Assay for Detection of *Escherichia coli* Heat-Labile Enterotoxin," J. Chin, Microbiol. 6: 439–444 (1977).

Primary Examiner—Esther L. Kepplinger
Assistant Examiner—Janelle Graeter
Attorney, Agent, or Firm—M. Howard Silverstein; Beverly K. Johnson; Curtis P. Ribando

[57] ABSTRACT

A crystal-violet dye binding technique useful for the detection and differentiation of virulent plasmid-bearing strains of *Yersinia enterocolitica*. Virulent plasmid-bearing strains of the bacteria bind the crystal violet dye to form dark violet colonies while avirulent plasmidless strains fail to bind the dye and remain white in color. The method is simple, rapid, economical and highly reliable.

15 Claims, 2 Drawing Sheets

**SIMPLE AND RAPID METHOD FOR DETECTION OF VIRULENT *YERSINIA ENTEROCOLITICA***

BACKGROUND OF THE INVENTION

1. Field of the Invention

The present invention relates to techniques for the detection of human pathogens in foods. More particularly, the present invention relates to a novel method useful for the detection and differentiation of virulent and avirulent strains of the bacterium *Yersinia enterocolitica* "*Y. enterocolitica*" using a crystal violet "CV" dye binding technique.

2. Description of the Prior Art

*Y. enterocolitica* is a potential human pathogen which has caused considerable concern in the food industry because of its ability to grow at refrigeration temperatures. Since its discovery over 40 years ago, the microorganism has been isolated from various food products including milk, milk products, egg products, raw meats, poultry and vegetables.

Various strains of *Y. enterocolitica* have been isolated. However, the disease-causing potential of the microorganism is associated with the virulent plasmid-bearing "P+" strains of *enterocolitica*. Consequently, the evaluation of foods as well as clinical and environmental samples for the presence of *Y. enterocolitica* requires the additional determination of the potential virulence of the strains isolated.

Presently, the evaluation of isolates of *Y. enterocolitica* requires either the use of sophisticated techniques such as radioactive DNA colony hybridization or plasmid profiling, or the use of clinical assessment techniques such as calcium dependency, serum resistance and autoagglutination. However, these techniques have proven to be impractical for field application. Besides being cumbersome, time consuming and expensive, clinical procedures are often not adaptable to large numbers of cultures and their results are often inconsistent. The colony hybridization technique requires the frequent preparation of the $^{32}P$-labeled DNA probe which is inconvenient and expensive. Further, the colony hybridization technique is potentially hazardous since the method requires the handling of millicurie levels of radioactive material.

Consequently, there exists a need for a method for the evaluation of foods, environmental and clinical samples for the pathogen *Y. enterocolitica*, which is easy, economical, reliable and safe.

SUMMARY OF THE INVENTION

We have now developed a CV dye binding method which is useful for the detection of virulent strains of *Y. enterocolitica* and for the differentiation between virulent and avirulent strains of the bacteria. In the assay of the invention, CV binds selectively to virulent $P^{30}$ strains of *Y. enterocolitica* but fails to bind avirulent plasmidless "P−" strains of the bacteria. The assay is rapid, safe, simple and highly effective.

Accordingly, it is an object of the present invention to provide a safe, simple, rapid and highly effective method for the detection of virulent P+ strains of *Y. enterocolitica*.

Another object of this invention is to provide a method for the detection of and differentiation between virulent P+ and avirulent P− strains of *Y. enterocolitica* which is more economical and less hazardous than prior known methods.

Still, another objective of this invention is to provide a method of quantifying the amount of virulent P+ colonies in mixed cultures of *Y. enterocolitica*.

For purposes of the invention, the term "mixed culture" is used herein to designate cultures of *Y. enterocolitica* which contain virulent P+ and avirulent P− strains of the bacteria. The abbreviation "CV+" and "CV−" is used herein to designate respectively strains of *Y. enterocolitica* which bind crystal violet dye and strains which fail to bind crystal violet dye.

In general, the method of the invention comprises treating colonies of *Y. enterocolitica* with an aqueous solution of CV dye for a period of time sufficient to allow the dye to bind to the virulent colonies of P+ strains; subsequently removing the dye solution from the bacteria colonies; and thereafter, visually detecting, i.e. determining the presence or absence of, virulent P+ strains of the colonies by their dark violet appearance in color due to binding with the dye. Avirulent P− strains, if any, present in the bacterial colonies are differentiated from the virulent P+ strains by their white appearance in color due to failure to bind with the dye. Further, the invention method allows one to quantify the number of virulent and avirulent colonies of *Y. enterocolitca* in a mixed culture by simply counting the number of colonies which bind or fail to bind the dye.

BRIEF DESCRIPTION OF THE DRAWINGS

FIG. 1 shows the results of the CV binding assay of the invention on individual virulent and avirulent colonies of *Y. enterocolitica* strain GER (serotype 0:3) when cells were grown on Brain Heart Infusion (BHI) agar for 30 hours at 37° C.

FIG. 1A indicates virulent P+ cells showing dark colonies.

FIG. 1B indicates avirulent P− cells showing white colonies.

FIG. 2 shows the results of CV binding assay of the invention on mixed virulent P+ and avirulent P− colonies of *Y. enterocolitica* strain GER (serotype 0:3) when cells were grown on BHI agar for 30 hours at 37° C.

DETAILED DESCRIPTION OF THE INVENTION

*Y. enterocolitica* stock cultures may be grown under aerobic conditions at any incubation temperature and time satisfactory for growth and plasmid stabilization of the bacteria. Generally, the cultures are incubated at 5° C. to 25° C., most preferably 25° C., for about 17 to 18 hours.

The media useful for growth of the *Y. enterocolitica* stock cultures is any nutrient media suitable to support growth and plasmid stability of the bacteria cells. For optimum growth and plasmid stability, the preferred media is BHI broth. The pH of the nutrient media suitable for growth of the organism is about neutrality, i.e., pH 6.7 to 7.2.

In accordance with the binding assay of the invention, stock cultures of *Y. enterocolitica* are plated on a nutrient rich media and incubated at a time and temperature sufficient to express plasmid genes in the virulent P+ strains which bind to crystal violet dye. The media may be any rich medium containing agar, preferably BHI agar. Colonies are preferably incubated at near 33° C. to near 40° C. for about 24 to 30 hours. For optimum results, colonies are incubated at about 35° C. to 37° C. for about 24 to 30 hours.

The CV dye solution useful in the invention assay consists of crystal violet dye dissolved in water, preferably distilled water. The aqueous dye solution may be used in any concentration sufficient to allow the virulent P+ colonies of the bacteria to bind the dye but insufficient to allow the medium plates or avirulent P− colonies to bind the dye. Exemplary concentrations of the aqueous dye solution useful in the method of the invention is from about 50 $\mu$g/ml to 200 $\mu$g/ml. The preferred concentration is from about 80 to 90 $\mu$g/ml. For optimum results, the most preferred concentration is 85 $\mu$g/ml. Reduced concentrations may result in a low color intensity in P+ cells while higher concentrations may produce high background color due to retention or binding of the dye on the media plates.

The CV binding assay of the invention is very rapid. Preferably, the culture plates are gently treated with the aqueous CV-dye solution for about 2 to 5 minutes. While low concentrations of dye solution may require additional time, it is desirable to perform all steps of the invention method within a maximum of 15 minutes since the distinct differentiation in pigmentation between the P+ and P− colonies of the bacteria diminishes with time.

The following examples are intended to further illustrate the invention and not to limit the scope of the invention as defined by the claims.

EXAMPLE 1

Strains of *Y. enterocolitica* GER (serotype 0:3) were grown in BHI broth with agitation for 18 hours at 25° C. The cells were diluted to a concentration of $10^3$ per ml and surface plated on BHI agar using a spiral plater. The plates were incubated for 30 hours at 37° C. Thereafter, the plates were gently flooded for 2 minutes with 8 ml of 85 $\mu$g/ml solution of CV dye in distilled water and the solution was decanted.

As shown in FIG. 1A, the P+ strains bound CV producing dark violet CV colonies after the cells were grown for 30 hours at 37° C. The avirulent P− colonies did not bind CV but remained white in color, as indicated in FIG. 1B. Colony morphology of CV+ and CV− strains examined by low magnification stereomicroscope were as follows: The CV+ strains were small, convex, shiny, dark opaque colonies. The CV− strains were shiny, translucent, flat white colonies.

EXAMPLE 2

The CV binding technique as described in Example 1 was assessed using five P+ strains of *Y. enterocolitica* and their P− derivatives representing four serotypes. P+ and P− strains of *Y. enterocolitica* GER (serotype 0:3) were used for standardization of optimum conditions. CV+ strains were examined for virulence and in vitro properties associated with virulence using the following tests:

ORAL INFECTION

Swiss Webster albino male mice (15–20 μg) were pretreated with 5 mg of iron-dextran. Virulence of P+ and P− strains were determined by examining for diarrhea following oral infection of the mice.

CALCIUM DEPENDENCY

Calcium dependence was tested by growth on agar containing magnesium oxalate.

AUTOAGGLUTINATION

Autoagglutination was determined by the method as described in W. J. Laird et al. [J. Clin. Microbiol. 11: 430–432 (1980)], using Eagle's minimal essential medium supplemented with 10% fetal bovine serum.

HYDROPHOBICITY

Hydrophobicity was examined by the method as described in R. V. Lachica et al. [J. Clin. Microbiol. 19: 660–663 (1984)].

CONGO RED PIGMENTATION

The Congo red acid-morpholinepropanesulfonic acid pigmentation agar was prepared as described in J. K. Prpic et al. [J. Clin. Microbiol. 18: 486–490 (1983)].

Results were analyzed and recorded in Table I.

The results of Table I show the usefulness of the CV binding technique of the invention to detect virulent P+ strains of *Y. enterocolitica*. As shown in Table I, all strains grown at 25° C. failed to bind CV dye while all P+ strains of the different serotypes grown at 37° C. responded positively to the CV binding screening test. The corresponding isogenic P− strains of *Y. enterocolitica* did not bind to CV when grown at 37° C. but remained whitish in appearance. Further, CV+ binding correlated with virulence as shown by oral infection causing diarrhea in iron-overloaded mice. Only CV+ WA serogroup (0:8) evoked clear-cut mouse lethality along with diarrhea. Respecting other virulence-associated properties, CV+ but not CV− strains displayed appropriate virulence-associated characteristics in every case except Congo red pigmentation. Both P+ isolates and their P derivatives gave red colonies on a Congo red containing medium.

EXAMPLE 3

The CV binding method of the invention was used to quantitatively detect and differentiate P+ strains from P− strains in mixed cultures of *Y. enterocolitica*.

The CV binding assay was as follows: Virulent P+ cells of *Y. enterocolitica* GER (serotype 0:3) were mixed in various ratios with cells from avirulent P− GER strains of the bacteria. The mixed cultures were surface plated on BHI agar and thereafter were incubated and treated in accordance with the assay as described in Example 1. Results were recorded in Table II.

As indicated by FIG. 2, CV selectively bound the virulent P+ strains as evidenced by dark colonies while failing to bind avirulent P− strains, colonies of which remain white in color. Calculated from the number of added P+ cells, the data shown in Table II clearly indicates the ability of the CV binding method of the invention to differentiate and quantify the number of individual P+ colonies present in mixed

TABLE I

Virulence and virulence-associated properties of plasmid-bearing strains of *Y. enterocolitica* and their plasmidless derivatives.

| Strain | Serotype | CV binding at 37° C. | CV binding at 25° C. | Diarrhea[b] (Mice) | CAD | AA | HP | CRAMP Agar | Plasmid (40-45 Md) |
|---|---|---|---|---|---|---|---|---|---|
| GER | 0:3 | + | − | + | + | + | + | + | + |
| GER-C | | − | − | − | − | − | − | + | − |
| EWMS | 0:3 | + | − | + | + | + | + | + | + |
| EWMS-C | | − | − | − | − | − | − | + | − |
| PT18-1 | 0:5,0:27 | + | − | + | + | + | + | + | + |
| PT18-1-C | | − | − | − | − | − | − | + | − |
| O:TAC | 0:TACOMA | + | − | + | + | + | + | + | + |
| O:TAC-C | | − | − | − | − | − | − | + | − |
| WA | 0:8 | + | − | + | + | + | + | + | + |
| WA-C | | − | − | − | − | − | − | + | − |

[b]Fecal material consistency was liquid; diarrhea was observed on days 4, 5, 6, 7 followed by death on 8th day post-infection in case of serogroup 0:8; for three other serogroups (0:3, 0:5, 0:27 and 0:TACOMA) diarrhea was observed on days 5, 6, 7 post-infection with no death.
CAD = Calcium dependency.
AA = Autoagglutination
HP = Hydrophobicity
CRAMP = Congo red acid-morpholinepropanesulfonic acid pigmentation.

Fecal material consistency was liquid; diarrhea was observed on days 4, 5, 6, 7 followed by death on 8th day post-infection in case of serogroup 0:8; for three other serogroups (0:3, 0:5, 0:27 and 0:TACOMA) diarrhea was observed on days 5, 6, 7 post-infection with no death. CAD=Calcium dependency. AA=Autoagglutination HP=Hydrophobicity CRAMP=Congo red acid-morpholinepropanesulfonic acid pigmentation.

TABLE II

Efficiency of CV binding in mixed cultures of virulent and avirulent strains.

| Sample | Estimated Number of Colonies Avirulent | Estimated Number of Colonies Virulent | Number of Virulent Colonies Observed (%) |
|---|---|---|---|
| A | 172 | — | 0 |
| B | 141 | 16 | 16 (100) |
| C | 131 | 31 | 29 (93) |
| D | 85 | 56 | 56 (100) |
| E | 72 | 98 | 92 (93) |
| F | 53 | 124 | 103 (83) |
| G | 22 | 130 | 124 (94) |
| H | — | 175 | 173 (98) |
| | | | Average 94.4% | cultures of *Y. enterocolitica*. The average efficiency of the assay was about 94.4%.

The method of the present invention is advantageous in that microscopic observation is not necessary to distinguish between virulent and avirulent strains of *Y. enterocolitica*. Further, permanent records of the results may be easily retained using photographs. This is especially recommended since CV dye may diffuse through the medium and unbound P+ colonies on standing over long periods of time. Additional advantageous features of the invention technique may be realized since the technique does not require special equipment and can be used effectively with large numbers of cultures.

It is understood that modifications and variations may be made to the foregoing disclosure without departing from the spirit and scope of the invention.

We claim:

1. A method for detecting a virulent plasmid-bearing strain of the bacterium *Yersinia enterocolitica* comprising:

a. incubating colonies of the bacterium at a time and temperature sufficient to express plasmid genes in said virulent strain, which strain binds crystal violet dye;

b. subsequently treating the colonies with an aqueous crystal violet dye solution for a period of time sufficient to allow the dye to bind to the virulent plasmid-bearing strain of the bacterium;

c. removing the dye solution from the colonies; and d. thereafter, detecting the virulent plasmid-bearing strain of the bacterium by the dark violet appearance in color of the colonies of said strain due to binding with the dye.

2. The method of claim 1 wherein the colonies are incubated at about 33°-40° C. for about 24-30 hours.

3. The method of claim 1 wherein the colonies are incubated at about 35°-37° C. for about 24-30 hours.

4. The method of claim 1 wherein the aqueous crystal violet dye solution is in a concentration in the range of about 50-200 $\mu g/ml$.

5. The method of claim 3 wherein the aqueous crystal violet dye solution is in a concentration of about 85 $\mu g/ml$.

6. A method for differentiating a virulent plasmid-bearing strain from an avirulent plasmidless strain of the bacterium *Yersinia enterocolitica* in a mixed culture of said strains comprising:

a. incubating the culture at a time and temperature sufficient to express plasmid genes in said virulent plasmid-bearing strain, which strain binds crystal violet dye;

b. subsequently treating the culture with an aqueous crystal violet dye solution for a period of time sufficient to allow the dye to bind to the virulent plasmid-bearing strain;

c. removing the dye solution from the culture; and d. thereafter, differentiating between the virulent plasmid-bearing strain and the avirulent plasmidless strain by the dark violet appearance of colonies of the virulent plasmid-bearing strain due to binding with the dye and the white appearance of colonies of the avirulent plasmidless strain due to failure to bind with the dye.

7. The method of claim 6 wherein the culture is incubated at about 33°-40° C. for about 24-30 hours.

8. The method of claim 6 wherein the culture is incubated at about 35°-37° C. for about 24-30 hours.

9. The method of claim 6 wherein the aqueous crystal violet dye solution is in a concentration in the range of about 50-200 $\mu g/ml$.

10. The method of claim 8 wherein the aqueous crystal violet dye solution is in a concentration of about 85 $\mu g/ml$.

11. A method for quantifying the amount of virulent plasmid-bearing strains in a culture of the bacterium *Yersinia enterocolitica* comprising:

a. incubating the culture at a time and temperature sufficient to express plasmid genes in said virulent plasmid-bearing strains which bind crystal violet dye;
b. subsequently treating the culture with an aqueous crystal violet dye solution for a period of time sufficient to allow the dye to bind to the virulent plasmid-bearing strains in the culture;
c. removing the dye solution from the culture; and
d. thereafter, counting the number of colonies of virulent plasmid-bearing strains in the culture by the dark violet appearance of the colonies of the virulent plasmid-bearing strain due to binding with the dye.

12. The method of claim 11 wherein the culture is incubated at about 33°-40° C. for about 24-30 hours.

13. The method of claim 11 wherein the culture is incubated at about 35°-37° C. for about 24-30 hours.

14. The method of claim 11 wherein the culture of *Yersinia enterocolitica* further comprises an avirulent plasmidless strain of *Yersinia enterocolitica* in addition to the virulent plasmid-bearing strain of the bacterium.

15. The method of claim 14 wherein the colonies of the avirulent plasmidless strain of the culture remains white in color following treatment of the culture with the aqueous crystal violet dye solution.

* * * * *

UNITED STATES PATENT AND TRADEMARK OFFICE
CERTIFICATE OF CORRECTION

PATENT NO. : 4,952,497
DATED : August 28, 1990
INVENTOR(S) : Saumya Bhaduri, Lucille K. Conway, and Reynato V. Lachica It is certified that error appears in the above-identified patent and that said Letters Patent is hereby corrected as shown below:

Column 1, line 58, delete "$P^{30}$" and insert -- $P^+$ -- .

Column 5, line 15, before footnote b insert the following:
--$^a$The strains designated with "-C" are the avirulent plasmidles derivatives ($P^-$) of the respective corresponding virulent strains ($p^+$) without the "-C" designation.--

Column 5, delete lines 20-25 (duplication of Table I footnotes).

Signed and Sealed this

Twenty-first Day of January, 1992

Attest:

HARRY F. MANBECK, JR.

*Attesting Officer*      *Commissioner of Patents and Trademarks*